United States Patent [19]
Zinnen et al.

[11] Patent Number: 6,137,024
[45] Date of Patent: Oct. 24, 2000

[54] PROCESS FOR SEPARATING META-XYLENE

[75] Inventors: Herman A. Zinnen, Evanston; Charles P. McGonegal, Addison, both of Ill.

[73] Assignee: UOP LLC, Des Plaines, Ill.

[21] Appl. No.: 09/255,101

[22] Filed: Feb. 22, 1999

Related U.S. Application Data

[63] Continuation-in-part of application No. 08/851,354, May 5, 1997, Pat. No. 5,877,373.

[51] Int. Cl.$^7$ .............................. C07C 7/12; C10G 25/00
[52] U.S. Cl. ...................... 585/828; 585/820; 208/310 Z
[58] Field of Search ....................... 208/310 Z; 585/828, 585/820

[56] References Cited

U.S. PATENT DOCUMENTS

| | | | |
|---|---|---|---|
| 2,836,633 | 5/1958 | Esmay et al. | 260/671 |
| 3,122,494 | 2/1964 | Brown et al. | 208/63 |
| 3,211,798 | 10/1965 | Burk, Jr. et al. | 260/668 |
| 3,793,385 | 2/1974 | Bond et al. | 260/674 SA |
| 3,903,187 | 9/1975 | Geissler | 260/674 SA |
| 4,313,015 | 1/1982 | Broughton | 585/828 |
| 4,368,347 | 1/1983 | Carra et al. | 585/828 |
| 4,554,398 | 11/1985 | Barthomeuf et al. | 585/828 |
| 4,584,424 | 4/1986 | Barthomeuf | 585/828 |
| 4,743,708 | 5/1988 | Rosenfeld et al. | 585/828 |
| 4,899,017 | 2/1990 | Yan | 585/328 |
| 4,940,830 | 7/1990 | Zinnen et al. | 585/828 |
| 5,030,787 | 7/1991 | Absil et al. | 585/475 |
| 5,171,922 | 12/1992 | Anderson | 585/805 |
| 5,177,280 | 1/1993 | Juguin et al. | 585/323 |
| 5,177,295 | 1/1993 | Oroskar et al. | 585/805 |
| 5,382,747 | 1/1995 | Kulprathipanja | 585/828 |
| 5,495,061 | 2/1996 | Kulprathipanja | 585/828 |
| 6,005,153 | 12/1999 | Zinnen et al. | 585/475 |
| 6,008,424 | 12/1999 | Zinnen et al. | 585/475 |

FOREIGN PATENT DOCUMENTS

| | | |
|---|---|---|
| 67656/90 | 11/1992 | Australia . |
| 2031096 | 3/1992 | Canada . |

*Primary Examiner*—Walter D. Griffin
*Assistant Examiner*—Tam M. Nguyen
*Attorney, Agent, or Firm*—John G. Tolomei; Frank S. Molinaro; Maryann Maas

[57] ABSTRACT

A process for separating meta-xylene from a mixture containing meta-xylene, para-xylene, and ortho-xylene has been developed. The process involves contacting the mixture with zeolite Beta to effect the adsorption of the para-xylene, ortho-xylene, and ethylbenzene in preference to the meta-xylene and recovering the meta-xylene.

14 Claims, 1 Drawing Sheet

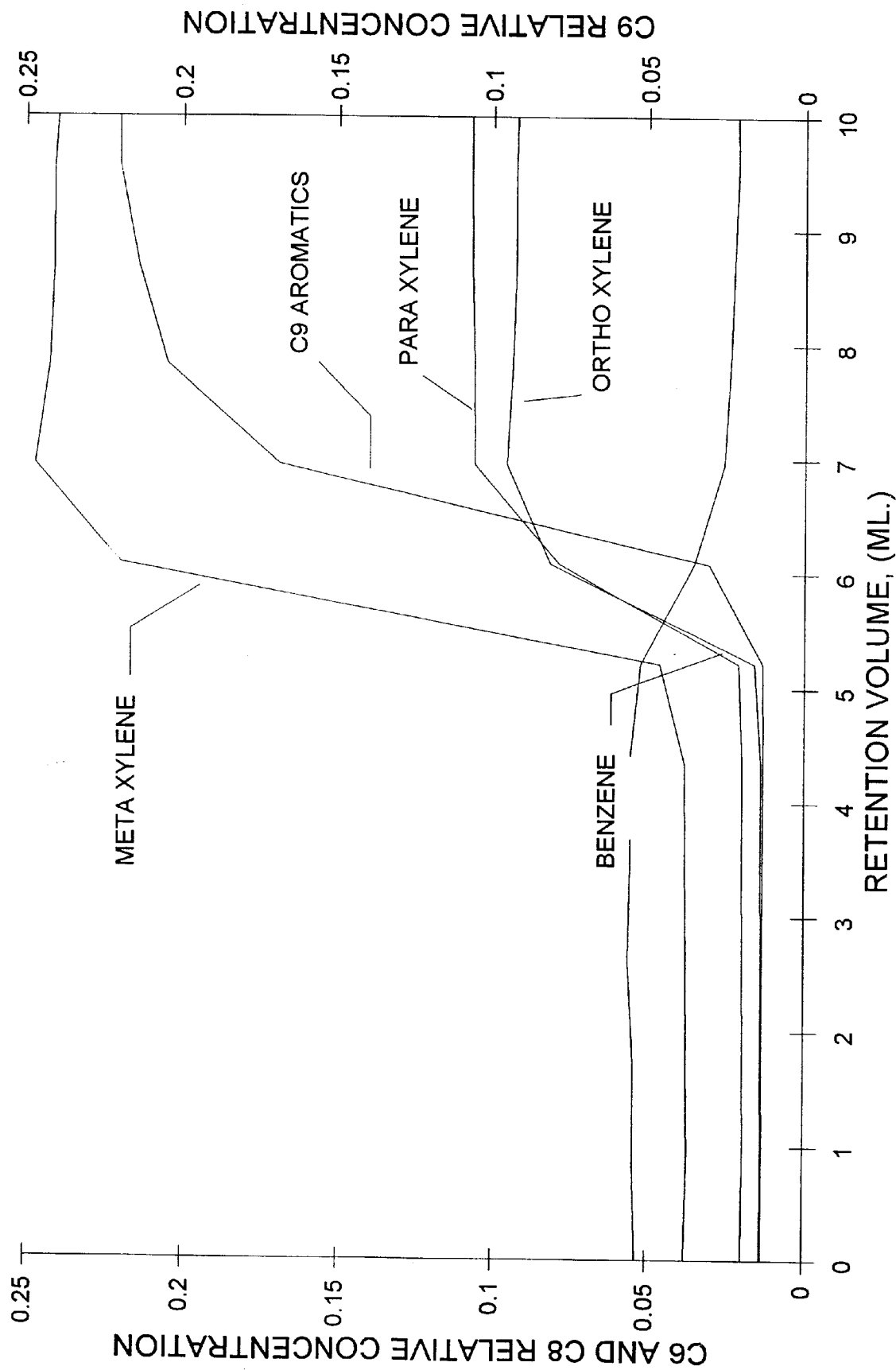

6,137,024

PROCESS FOR SEPARATING META-XYLENE

CROSS REFERENCE TO RELATED APPLICATION

This application is a continuation-in-part of our application Ser. No. 08/851,354, filed May 5, 1997, now U.S. Pat. No. 5,877,373, all of which is hereby incorporated by reference.

BACKGROUND OF THE INVENTION $C_8$ alkylaromatic hydrocarbons are generally considered to be valuable products, with the demand for para-xylene being high and the demand for meta-xylene steadily increasing. In typical $C_8$ alkylaromatic hydrocarbon formation processes, the reaction product contains a mixture of ethylbenzene, ortho-xylene, meta-xylene, and para-xylene. Therefore, the desired $C_8$ alkylaromatic hydrocarbon isomer must be separated from the mixture. Historically, industry has sought ways to separate para-xylene, the most desired compound, from the mixture, and numerous patents exist to that end. For example, zeolites X and Y have been used to selectively adsorb para-xylene; see U.S. Pat. No. 3,903,187, U.S. Pat. No. 4,313,015, U.S. Pat. No. 5,171,922, U.S. Pat. No. 5,495,061 and U.S. Pat. No. 5,177,295. Similarly, U.S. Pat. No. 4,899,017 discloses contacting the $C_8$ alkylaromatic hydrocarbon mixture with a zeolitic adsorbent selective for para-xylene and then contacting the adsorbent with a nonaqueous desorbent to recover the para-xylene from the adsorbent. The stated zeolitic adsorbents selective for para-xylene in U.S. Pat. No. 4,899,017 are ZSM-5, ZSM-11 and zeolite Beta. U.S. Pat. No. 4,940,830 discloses a rejective separation of para-xylene from other xylene isomers and ethylbenzene using sodium Y zeolite or a sodium Y zeolite ion exchanged with an element from Groups IB or VII of the Periodic Table.

With growing interest in meta-xylene, patents directed to the separation of meta-xylene are becoming more numerous. For example, U.S. Pat. No. 5,382,747 discloses adsorbing meta-xylene using a sodium or sodium and lithium exchanged Y zeolite to separate meta-xylene from a mixture of $C_8$ aromatic hydrocarbons including other xylenes in the liquid phase. U.S. Pat. No. 4,368,347 discloses a rejective separation of meta-xylene using zeolite Y preliminarily exchanged with potassium.

Applicants have discovered that a particular adsorbent, zeolite Beta, is effective in separating meta-xylene from a mixture of $C_8$ alkylaromatic hydrocarbons. Zeolite Beta has been used to separate isomers of $C_9$ aromatic hydrocarbons (U.S. Pat. No. 4,554,398) and $C_{10}$ aromatic hydrocarbons (U.S. Pat. No. 4,743,708). Zeolite Beta has also been used to selectively adsorb ethylbenzene from a stream containing ethylbenzene and one or more isomeric xylenes, (U.S. Pat. No. 4,584,424) and to selectively adsorb para-xylene from a stream containing para-xylene and another $C_8$ aromatic hydrocarbon (U.S. Pat. No. 4,899,617). Applicants have discovered that zeolite Beta is uniquely suited to the separation of meta-xylene from other xylene isomers since zeolite Beta preferentially rejects meta-xylene as compared to the other xylene isomers. Therefore, the meta-xylene of a mixture of xylene isomers that is in contact with zeolite Beta will be carried with the fluid flow, while the other isomers are retained by the zeolite Beta thereby allowing for the recovery of separated meta-xylene.

SUMMARY OF THE INVENTION

The purpose of the invention is to provide a process for separating meta-xylene from a mixture containing meta-xylene, para-xylene, and ortho-xylene. Ethylbenzene may also be present in the mixture. The process involves contacting the mixture with zeolite Beta to effect the adsorption of the para-xylene, ortho-xylene, and ethylbenzene in preference to the meta-xylene and recovering the meta-xylene. The process may also involve contacting a desorbent with the zeolite Beta to desorb the adsorbed para-xylene, ortho-xylene, and ethylbenzene with preferred desorbents being toluene, benzene, or a combination thereof. In another embodiment of the invention, the mixture may additionally contain at least one $C_9$ or $C_{10}$ alkylaromatic hydrocarbon with the $C_9$ or $C_{10}$ alkylaromatic hydrocarbon being adsorbed in preference to the meta-xylene.

BRIEF DESCRIPTIONS OF THE DRAWING

The FIGURE is a chromatographic plot of the concurrent transalkylation of 1,3,5-trimethylbenzene and separation of the $C_8$ alkylaromatic hydrocarbon products using zeolite Beta as both the catalyst and adsorbent as described in the example. Each individual isomer of the $C_8$ alkylaromatic hydrocarbons is plotted and the $C_9$ alkylaromatic hydrocarbons are summed and the sum of the concentrations is plotted.

DETAILED DESCRIPTION OF THE INVENTION

In general terms, the invention involves using zeolite Beta as an adsorbent in a separation process to separate meta-xylene from a mixture containing at least meta-xylene, para-xylene, and ortho-xylene. The mixture may also contain ethylbenzene, $C_9$ alkylaromatic hydrocarbons and/or $C_{10}$ alkylaromatic hydrocarbons. Zeolite Beta preferentially adsorbs the para-xylene, ortho-xylene, ethylbenzene, and $C_9$ and $C_{10}$ alkylaromatic hydrocarbons as compared to meta-xylene. In other words, the zeolite Beta preferentially rejects meta-xylene. Therefore, as the mixture contacts the zeolite Beta, the meta-xylene will be carried with the fluid flow and recovered from the process. The ortho-xylene, para-xylene, ethylbenzene, and $C_9$ and $C_{10}$ alkylaromatic hydrocarbons will be adsorbed by the zeolite Beta and their flow through the adsorbent hindered, thereby being separated from the meta-xylene. The meta-xylene is recovered as the desired product of the separation. Optionally, the adsorbed hydrocarbons may be desorbed from the zeolite Beta using a desorbent to regenerate the zeolite Beta for continued use.

The adsorbent used in the present invention is zeolite Beta. Zeolite Beta is a well known zeolite whose structure is defined by the Structure Commission of the International Zeolite Association under the code BEA in Meier, W. M., Olson, D. H. and Baerlocher, Ch. *Atlas of Zeolite Structure Types*, 4th revised edition; Elsiver: New York, 1996, p. 62–3. Various different forms of zeolite Beta are known having a range of silica to alumina ratios. Suitable silica to alumina ratios for the zeolite Beta include from about 10 to about 200. When bound with suitable binding material, zeolite Beta can be formed into various shapes such as spheres, cylinders and irregular granules. For purposes of this invention, particles sizes of the bound zeolite Beta can range from about 420 microns to about 840 microns. A uniform size distribution is preferred.

The process may be a batch process or a continuous process, with the continuous process being preferred. The separation using zeolite Beta may be conducted in a number of modes including: fixed bed, swing bed, moving bed, and simulated moving bed. The particular mode chosen is dependent upon the application, but generally the simulated moving bed is the preferred mode. The simulated moving bed mode is well known in industry and is not described in detail here. U.S. Pat. No. 4,940,830, incorporated by reference, provides greater detail regarding the simulated moving bed mode. U.S. Pat. No. 4,940,830, however, is directed to the separation of para-xylene from at least one other xylene isomer where the adsorbent is a sodium exchanged Y zeolite or a sodium exchanged Y zeolite further exchanged with a Group IB or Group VII element.

The separation process may be carried out under vapor phase conditions. Generally, for vapor phase operation, temperatures in the range of from about 120° C. to about 300° C. are suitable with pressures imposed so as to maintain the vapor phase. The preferred temperature range is from about 120° C. to about 250° C., and the preferred pressure is from about 69 kPag (10 psig) to about 345 kPag (50 psig).

The selective rejection of meta-xylene by the zeolite Beta allows for the recovery of meta-xylene from the mixture of xylene isomers. However, due to the zeolite Beta selectively adsorbing para-xylene and ortho-xylene, it may be beneficial to regenerate the zeolite Beta using a desorbent. The desorbent functions to desorb the adsorbed compounds such as para-xylene, ortho-xylene, ethylbenzene, and $C_9$ and $C_{10}$ alkylaromatic hydrocarbons from the zeolite Beta. The desorbed compounds are removed, and the regenerated zeolite Beta has renewed capacity for adsorbing additional compounds. It is preferred to regenerate the zeolite Beta prior to the saturation of the capacity of the adsorbent so as to prevent break-through of compounds such as para-xylene, ortho-xylene, ethylbenzene, and $C_9$ and $C_{10}$ alkylaromatic hydrocarbons which would contaminate the desired meta-xylene. The desorbent is any fluid capable of removing selectively adsorbed compounds from the adsorbent. Preferred desorbents include toluene, benzene, or a mixture of toluene and benzene.

EXAMPLE

A 70 cc column was loaded with 32.1 grams of a single 20–40 mesh compound which is capable of functioning both as a catalyst and as an adsorbent, zeolite Beta bound with alumina and in the hydrogen form. Zeolite Beta has the additional unique characteristic of selectively adsorbing para-xylene and ortho-xylene as compared to meta-xylene. The column was placed in a heated enclosure at 250° C. and maintained at a process pressure of 193 kPag (28 psig) using back pressure regulators. Toluene desorbent and hydrogen were directed into the columns at measured rates. A 20 cc pulse of 1,3,5-trimethylbenzene feed was introduced and the desorbent flow was resumed. Since zeolite Beta is a catalyst as well as an adsorbent, the toluene and the 1,3,5-trimethylbenzene were first catalytically transalkylated to form a mixture of $C_8$ alkylaromatic hydrocarbons. Then, through continued contact with the zeolite Beta, the mixture of $C_8$ alkylaromatic hydrocarbons underwent separation of the meta-xylene. The effluent of the system was condensed and analyzed by gas chromatography to obtain the composition of the effluent. The FIGURE shows the concentration profiles of the effluent beginning with the background level of toluene desorbent and the individual $C_8$ alkylaromatic hydrocarbons species, para-xylene, meta-xylene and ortho-xylene, as well as the sum of the $C_9$ alkylaromatic hydrocarbons. The background level of $C_8$ alkylaromatic hydrocarbons is due to toluene disproportionation. Because of zeolite Beta's unique characteristic of selectively adsorbing para-xylene and ortho-xylene as compared to meta-xylene, the FIGURE shows the first eluting compound to be meta-xylene, with the meta-xylene being significantly resolved from the para-xylene and ortho-xylene.

What is claimed is:

1. A process for separating meta-xylene from a mixture comprising meta-xylene, para-xylene, and ortho-xylene, said process comprising contacting the mixture with zeolite Beta in the hydrogen form to effect the adsorption of the para-xylene and ortho-xylene in preference to the meta-xylene and recovering the meta-xylene.

2. The process of claim 1 further comprising contacting a desorbent with the zeolite Beta in the hydrogen form to desorb the adsorbed para-xylene and ortho-xylene.

3. The process of claim 2 wherein the desorbent is selected from the group consisting of toluene, benzene, and a combination thereof.

4. The process of claim 1 wherein the mixture further comprises ethylbenzene which is adsorbed by the zeolite Beta in the hydrogen form in preference to the meta-xylene.

5. The process of claim 4 further comprising contacting a desorbent with the zeolite Beta in the to desorb the adsorbed para-xylene, ortho-xylene, and ethylbenzene.

6. The process of claim 5 wherein the desorbent is selected from the group consisting of toluene, benzene, and a combination thereof.

7. The process of claim 1 wherein the mixture further comprises at least one $C_9$ or $C_{10}$ alkylaromatic hydrocarbon, said $C_9$ or $C_{10}$ alkylaromatic hydrocarbon being adsorbed by the zeolite Beta in the hydrogen form in preference to the meta-xylene.

8. The process of claim 7 further comprising contacting a desorbent with the zeolite Beta in the hydrogen form to desorb the adsorbed para-xylene, ortho-xylene and $C_9$ or $C_{10}$ alkylaromatic hydrocarbon.

9. The process of claim 8 wherein the desorbent is selected from the group consisting of toluene, benzene, and a combination thereof.

10. The process of claim 1 wherein the mixture further comprises ethylbenzene and at least one $C_9$ or $C_{10}$ alkylaromatic hydrocarbon, said ethylbenzene and $C_9$ or $C_{10}$ alkylaromatic hydrocarbon being adsorbed by the zeolite Beta in the hydrogen form in preference to the meta-xylene.

11. The process of claim 10 further comprising contacting a desorbent with the zeolite Beta in the hydrogen form to desorb the adsorbed para-xylene, ortho-xylene, ethylbenzene and $C_9$ or $C_{10}$ alkylaromatic hydrocarbon.

12. The process of claim 11 wherein the desorbent is selected from the group consisting of toluene, benzene, and a combination thereof.

13. The process of claim 1 wherein said process is conducted at a temperature in the range of from about 120° C. to about 300° C.

14. The process of claim 1 wherein said process is conducted at a temperature in the range of from about 120° C. to about 250° C. and a pressure in the range of from about 69 kPag (10 psig) to about 345 kPag (50 psig).

* * * * *